US010506915B2

(12) United States Patent
Iwasaki et al.

(10) Patent No.: US 10,506,915 B2
(45) Date of Patent: Dec. 17, 2019

(54) SIGNAL PROCESSING APPARATUS AND ENDOSCOPE SYSTEM

(71) Applicant: OLYMPUS CORPORATION, Tokyo (JP)

(72) Inventors: Tomoki Iwasaki, Fuchu (JP); Tatsuhiko Suzuki, Hino (JP); Susumu Hashimoto, Hachioji (JP); Yuji Kutsuma, Kokubunji (JP); Toshihiro Hamada, Fuchu (JP); Hironori Nakagawa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/797,581

(22) Filed: Oct. 30, 2017

(65) Prior Publication Data
US 2018/0042454 A1    Feb. 15, 2018

Related U.S. Application Data

(63) Continuation of application No. PCT/JP2016/054024, filed on Feb. 10, 2016.

(30) Foreign Application Priority Data
Sep. 18, 2015   (JP) .................. 2015-185261

(51) Int. Cl.
A61B 1/00    (2006.01)
A61B 1/05    (2006.01)
(Continued)

(52) U.S. Cl.
CPC ...... A61B 1/00009 (2013.01); A61B 1/00006 (2013.01); A61B 1/00011 (2013.01);
(Continued)

(58) Field of Classification Search
CPC .................................. A61B 1/00009
See application file for complete search history.

(56) References Cited

U.S. PATENT DOCUMENTS 6,217,519 B1 *   4/2001   Grund ............... A61B 8/06
                                              600/463
6,669,628 B2 *  12/2003   Abe ................. A61B 1/045
                                              348/69
(Continued)

FOREIGN PATENT DOCUMENTS

JP    2003038432 A    2/2003
JP    2007307018 A   11/2007

OTHER PUBLICATIONS

Evaluation of contrast limited adaptive histogram; enhancement on a FPGA; Ferguson; 2008 (Year: 2008).*
(Continued)

Primary Examiner — Luis Perez-Fuentes
(74) Attorney, Agent, or Firm — Scully, Scott, Murphy & Presser, P.C.

(57) ABSTRACT

A first signal processing apparatus, to which a first endoscope apparatus including a first image sensor is detachably attached and communicably connected with a second signal processing apparatus to which a second endoscope apparatus including a second image sensor is attached, the first signal processing apparatus being configured to process a first imaging signal generated by the first image sensor or a second image signal generated by the second image sensor, includes a control unit configured to control a process inside the first signal processing apparatus in accordance with communication with the second signal processing apparatus. The control unit processes the first imaging signal when a first command is received, and when a second command is received, the control unit controls the process inside the first
(Continued)

signal processing apparatus to make the process of the second imaging signal to correspond to the second command.

6 Claims, 14 Drawing Sheets

(51) Int. Cl.
    *A61B 1/045*     (2006.01)
    *G02B 23/24*     (2006.01)

(52) U.S. Cl.
    CPC .......... *A61B 1/00059* (2013.01); *A61B 1/045* (2013.01); *A61B 1/05* (2013.01); *G02B 23/2476* (2013.01)

(56) References Cited

U.S. PATENT DOCUMENTS

| | | | |
|---|---|---|---|
| 8,915,838 B2* | 12/2014 | Ozaki | G06F 19/321 600/118 |
| 9,841,280 B2* | 12/2017 | Amling | G01C 11/04 |
| 9,912,911 B2* | 3/2018 | King | H04N 5/23225 |
| 2003/0197781 A1* | 10/2003 | Sugimoto | A61B 1/04 348/72 |
| 2005/0231591 A1* | 10/2005 | Abe | G09G 5/006 348/65 |
| 2014/0184766 A1* | 7/2014 | Amling | G01C 11/04 348/65 |

OTHER PUBLICATIONS

NPL Google Search; 2019; (Year: 2019).*
International Search Report dated Apr. 26, 2016 issued in PCT/JP2016/054024.

* cited by examiner

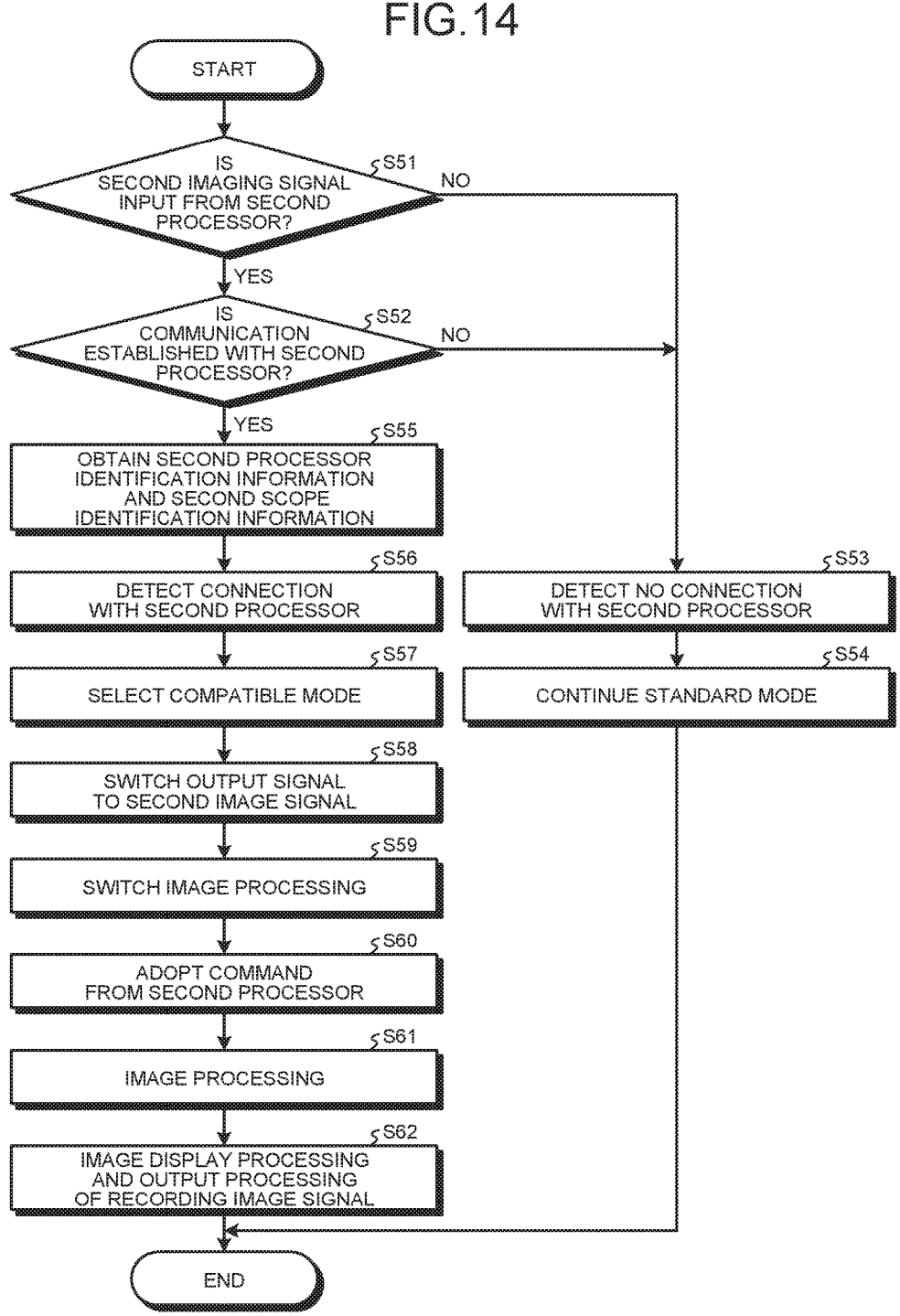

SIGNAL PROCESSING APPARATUS AND ENDOSCOPE SYSTEM

CROSS-REFERENCE TO RELATED APPLICATION

This application is a continuation of PCT international application Ser. No. PCT/JP2016/054024 filed on Feb. 10, 2016 which designates the United States, incorporated herein by reference, and which claims the benefit of priority from Japanese Patent Applications No. 2015-185261, filed on Sep. 18, 2015, incorporated herein by reference.

BACKGROUND

The present disclosure relates to a signal processing apparatus and an endoscope system.

In the medical field, an endoscope system is used for observing internal portions of a subject. The endoscope typically inserts an insertion unit having a thin and long shape into a subject such as a patient, emits illumination light supplied by a light source apparatus from a distal end of the insertion unit, and receives reflected light of the illumination light by an image sensor, thereby capturing an in-vivo image. The in-vivo image captured by the image sensor of the endoscope undergoes predetermined image processing by a signal processing apparatus (processor) of the endoscope system, and thereafter is displayed on a display of the endoscope system. A user such as a doctor observes an internal organ of the subject based on the in-vivo image displayed on the display.

In endoscopic inspection, since various endoscopes are appropriately used in accordance with the purpose of observation and an observed region, a plurality of endoscopes is used in combination in some cases. An endoscope system includes a processor, a display, and a recording apparatus as a set for individual types of endoscopes. Therefore, in a case of using a plurality of endoscopes in combination, a plurality of sets of processors, displays, and recording apparatuses is installed in accordance with each of the endoscopes. This results in complication of a wiring structure among the apparatuses and a necessity to ensure a wide area for installation, leading to enlargement of the entire system. In order to simplify the configuration of the entire system, there is a proposed configuration in which two processors are connected to each other, and one of the processors performs as a parent device output of image information to a display or a recording apparatus, thereby sharing the display or the recording apparatus by a plurality of processors (for example, refer to JP 2003-038432 A).

SUMMARY

A first signal processing apparatus according to one aspect of the present disclosure, to which a first endoscope apparatus including a first image sensor is detachably attached and communicably connected with a second signal processing apparatus to which a second endoscope apparatus including a second image sensor is attached, the first signal processing apparatus being configured to process a first imaging signal generated by the first image sensor or a second image signal generated by the second image sensor, may include a control unit configured to control a process inside the first signal processing apparatus in accordance with communication with the second signal processing apparatus, wherein the control unit processes the first imaging signal when a first command is received, and when a second command is received, the control unit controls the process inside the first signal processing apparatus to make the process of the second imaging signal to correspond to the second command.

An endoscope system according to another aspect of the present disclosure may include: a first signal processing apparatus to which a first endoscope apparatus including a first image sensor is detachably attached; and a second signal processing apparatus to which a second endoscope apparatus including a second image sensor is attached, wherein the first signal processing apparatus and the second signal processing apparatus are communicably connected, the endoscope system processing a first imaging signal generated by the first image sensor or a second image signal generated by the second image sensor, the first signal processing apparatus includes a control unit configured to control processing inside the first signal processing apparatus in accordance with communication with the second signal processing apparatus, the control unit processes the first imaging signal when a first command is received, and when a second command is received, the control unit controls the process inside the first signal processing apparatus to make the process of the second imaging signal to correspond to the second command.

The above and other objects, features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 14 is a flowchart illustrating setting of a standard mode or a compatible mode by the control unit of the first processor illustrated in FIG. 13 and a processing procedure of control processing of internal processing of the first processor in accordance with individual modes.

DETAILED DESCRIPTION

Figure 1:
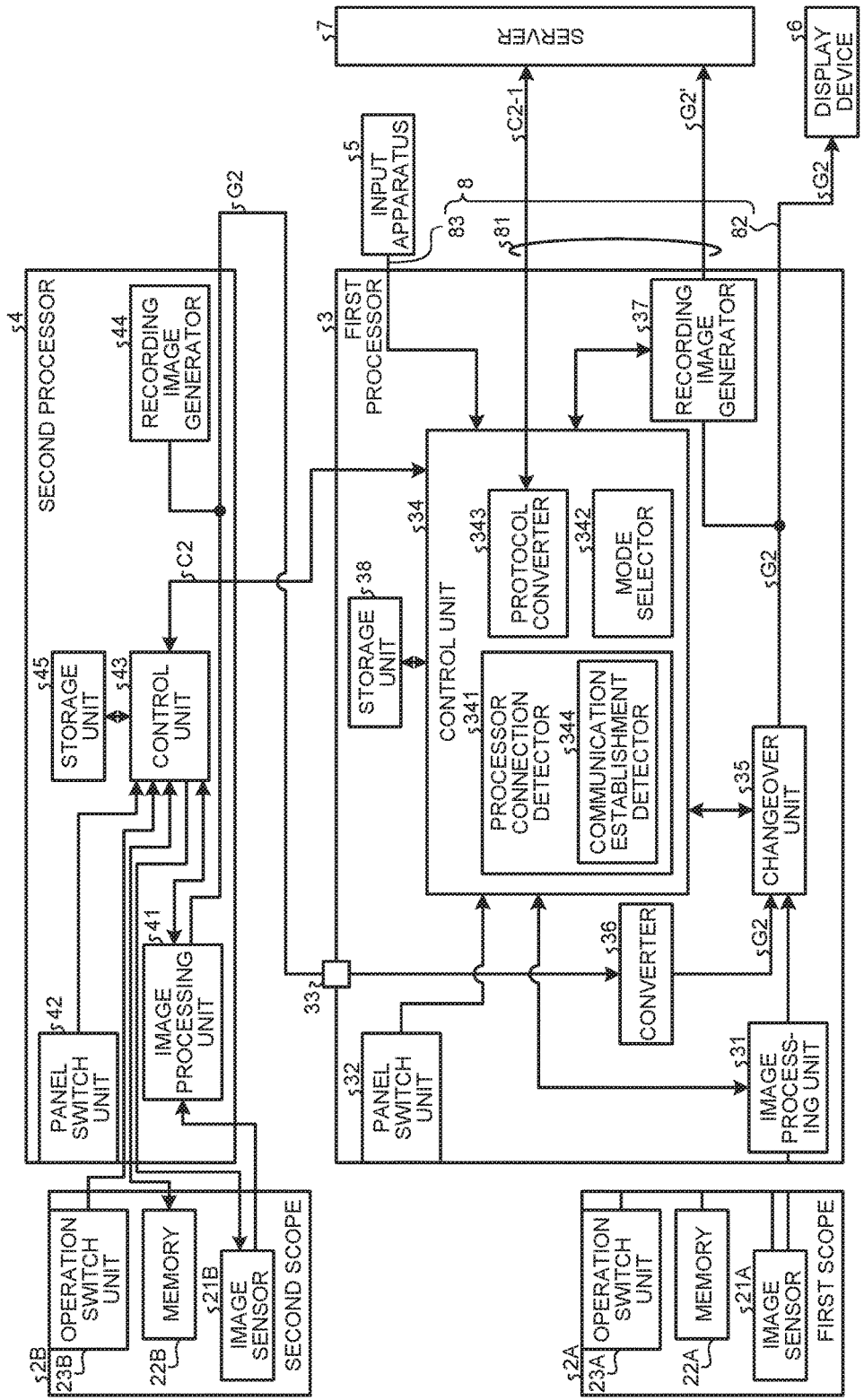
FIG. 1 is a schematic diagram illustrating a general configuration of an endoscope system according to a first embodiment of the present disclosure.

Hereinafter, a signal processing apparatus (processor) of an endoscope system will be described according to embodiments of the present disclosure (hereinafter, referred to as "embodiment(s)"). Note that the present disclosure is not intended to be limited by these embodiments. In the drawings, same reference signs are attached to the same portions.

First Embodiment

Figure 2:
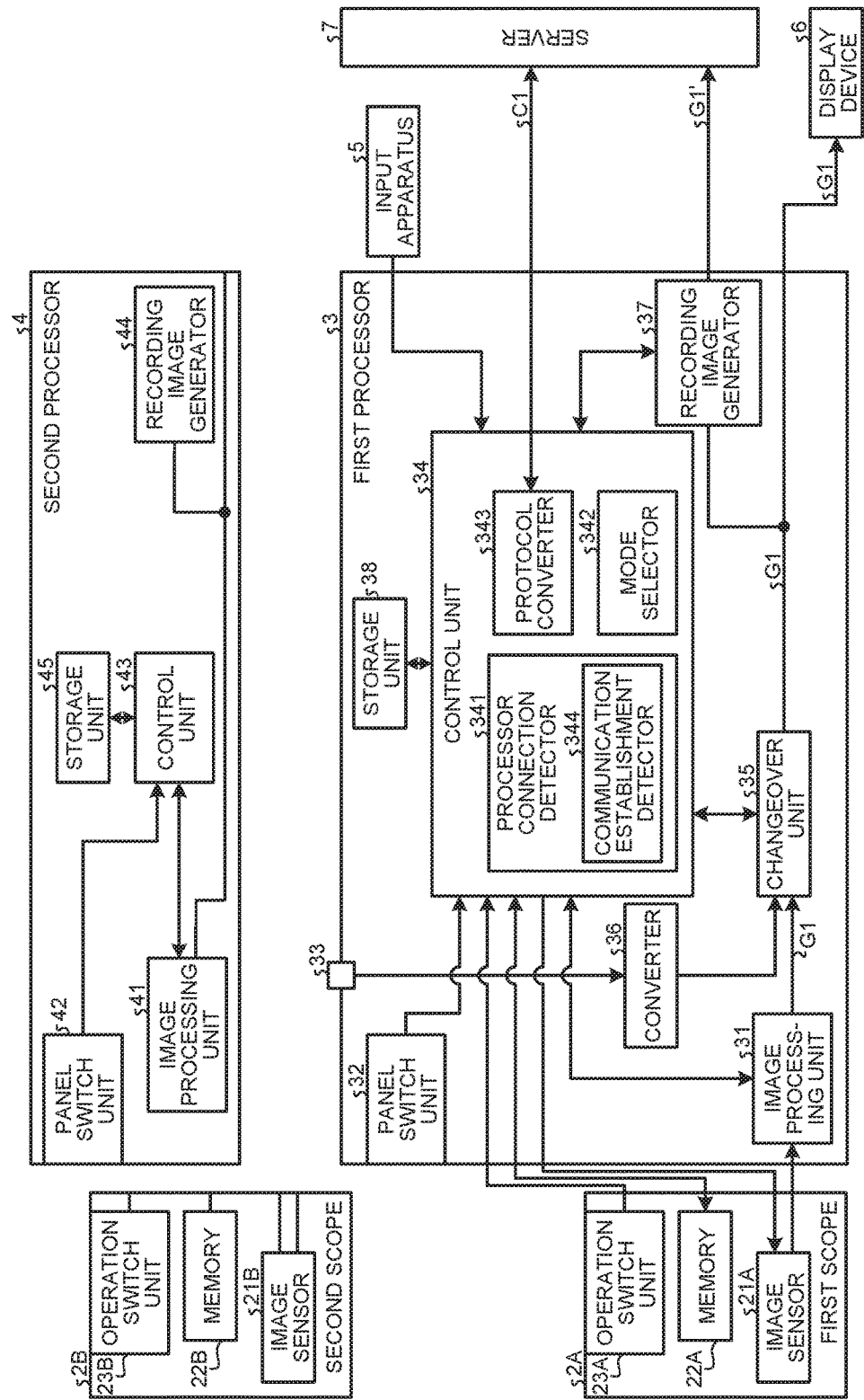
FIG. 2 is a schematic diagram illustrating a general configuration of an endoscope system according to the first embodiment of the present disclosure.

FIGS. 1 and 2 are schematic diagrams each illustrating a general configuration of an endoscope system according to a first embodiment of the present disclosure.

As illustrated in FIGS. 1 and 2, the endoscope system according to the first embodiment uses, as an endoscope (scope) to be introduced into a subject, a first scope 2A attachable to a first processor 3 (signal processing apparatus, first signal processing apparatus) or a second scope 2B attachable to a second processor 4 (another signal processing apparatus, second signal processing apparatus), for example. The endoscope system according to the first embodiment includes the first processor 3, the second processor 4, an input apparatus 5, a display device 6, and a server 7. The first processor 3 performs predetermined image processing on an imaging signal transmitted from the attached first scope 2A. The second processor 4 performs predetermined image processing on an imaging signal transmitted from the attached second scope 2B. The input apparatus 5 receives an input of various types of instruction information and inputs the received instruction information into the first processor 3. The display device 6 displays a video image corresponding to an image signal obtained by one of the first scope 2A and the second scope 2B. The server 7 is connected to and communicates with the first processor 3 via a network, or the like, and records various types of information. In the first embodiment, the first processor 3 is communicably connected with the second processor 4 to which the second scope 2B is attached, and also is connected to the input apparatus 5 and the display device 6. The first processor 3 has compatibility with the second processor 4 and controls processing inside the first processor 3 in accordance with communication with the second processor 4. With this configuration, the input apparatus 5 and the display device 6 are shared by the first processor 3 and the second processor 4.

Each of the first scope 2A and the second scope 2B is introduced into the subject and generates an image signal of an internal portion of the subject by imaging the internal portion of the subject. The first scope 2A is connected to the first processor 3 (refer to FIG. 2), and the second scope 2B is connected to the second processor 4 (refer to FIG. 1).

The first scope 2A includes, at its distal end portion, an image sensor 21A (first image sensor), a memory 22A, and an operation switch unit 23A including various operation switches such as a release switch. The second scope 2B includes, at its distal end portion, an image sensor 21B (second image sensor), a memory 22B, and an operation switch unit 23B including various operation switches such as a release switch.

Examples of the image sensors 21A and 21B include a CCD image sensor and a CMOS image sensor. A light receiving surface of the image sensor includes a plurality of pixels arranged in a matrix. Each of the pixels receives light from the subject onto which light is emitted and generates an imaging signal by photoelectrically converting the received light. In a case where the first scope 2A is attached to the first processor 3 (refer to FIG. 2), the image sensor 21A performs noise reduction processing, clamp processing, and A/D conversion processing onto a first imaging signal (analog) generated by the plurality of pixels, and outputs the signal as a first imaging signal (digital) to the first processor 3 via an electric cable (not illustrated). In a case where the second scope 2B is attached to the second processor 4 (refer to FIG. 1), the image sensor 21B performs noise reduction processing, clamp processing, and A/D conversion processing onto a second imaging signal (analog) generated by the plurality of pixels, and outputs the signal as a second imaging signal (digital) to the second processor 4 via an electric cable (not illustrated).

The memories 22A and 22B record the identification information and the model numbers of the first scope 2A and the second scope 2B, the type of the image sensors 21A and 21B, or the like. The memories 22A and 22B may record various parameters for image processing on the imaging signals captured by the image sensors 21A and 21B, such as parameters for white balance (WB) adjustment. In a case where the first scope 2A is attached to the first processor 3, the various types of information recorded by the memory 22A is output to a control unit 34 of the first processor 3 by communication processing with the first processor 3 via an electric cable (not illustrated). In a case where the second scope 2B is attached to the second processor 4, the various types of information recorded by the memory 22B is output to a control unit 43 of the second processor 4 by communication processing with the second processor 4 via an electric cable (not illustrated).

Each of the operation switch units 23A and 23B includes a plurality of buttons for operating the first processor 3, the second processor 4, and peripheral equipment such as an air supply apparatus, a water supply apparatus, and a gas supply apparatus. Each of the operation switch units 23A and 23B includes a release button. In a case where the release button is pressed during scope inspection, each of the operation switch units 23A and 23B inputs a release signal into the control unit 43 of the second processor 4 to be described below. The release signal instructs generation of still image data (release image data) from the image displayed on the display device 6 when the release button is pressed. In accordance with the input of the release signal, a recording image generator 37 to be described below generates release image data based on the video image displayed on the display device 6 at the input timing of the release signal. A bending knob for bending the first scope 2A and the second scope 2B and an insertion port for inserting a treatment instrument are provided in the vicinity of the operation switch units 23A and 23B.

The first scope 2A is detachably attached to the first processor 3 (refer to FIG. 2). The first processor 3 generates a first image signal by performing predetermined image processing on the first imaging signal transmitted from the attached first scope 2A. The first processor 3 is also communicably connected with the second processor 4. The first processor 3 transmits the command transmitted from the second processor 4, to the server 7. The first processor 3 outputs a second image signal input from the second processor 4 to the display device 6, generates a recording image signal from the second image signal, and outputs the generated signal to the server 7. The first processor 3 includes an image processing unit 31, a panel switch unit 32, an external video image input port 33, the control unit 34, a changeover unit 35 (selector), a converter 36, a recording image generator 37, and a storage unit 38.

The image processing unit 31 performs predetermined image processing on the first imaging signal generated by the image sensor 21A of the first scope 2A. The image processing unit 31 generates the first image signal by performing optical black subtraction (OB) processing, demosaicing processing, white balance (WB) adjustment processing, electronic zoom processing, edge enhancement processing, mask processing and on-screen display (OSD) processing, etc., on the first imaging signal (digital) generated by the image sensor 21A, and outputs the first image signal after converting it into a format that can be displayed on the display device 6. Note that there is a case where the image processing unit 31, instead of the image sensor 21A, performs noise reduction processing, clamp processing, and A/D conversion processing on the first imaging signal (analog).

The panel switch unit 32 is a switch group provided on a front panel constituting a casing of the first processor 3. In a case where the first scope 2A is attached to the first processor 3, the panel switch unit 32 receives an input of signals for freeze, release, and image adjustment (emphasis, electronic enlargement, color tone, etc.) onto the in-vivo image captured by the first scope 2A, and outputs the received various signals to the control unit 34 (refer to FIG. 2).

The second image signal output from an image processing unit 41 of the second processor 4 is input into the external video image input port 33 when the first processor 3 is connected with the second processor 4.

The control unit 34 includes a CPU. The control unit 34 controls processing operation of each of portions of the first processor 3 by performing operation including transfer of instruction information and data to each of components of the first processor 3. In a case where the first scope 2A is attached to the first processor 3, the control unit 34 is connected to the image sensor 21A and the memory 22A of the first scope 2A via individual cables, and controls the image sensor 21A and the memory 22A (refer to FIG. 2).

The control unit 34 is communicably connected to the server 7 via a network, or the like. Communication is performed between the first processor 3 and the server 7 using a first protocol. The control unit 34 is communicably connected to the control unit 43 of the second processor 4 via a cable. Communication is performed between the first processor 3 and the second processor 4 using a second protocol. The control unit 34 controls processing inside the first processor 3 in accordance with the communication with the second processor 4. The control unit 34 includes a processor connection detector 341, a mode selector 342, and a protocol converter 343. Both the first protocol and the second protocol are master-slave type communication protocols. The first processor 3 functions as a master in a master-slave system with the server 7 as an external device other than the second processor 4, and functions as a slave in the master-slave system with the second processor 4.

The processor connection detector 341 detects whether the first processor 3 is connected with the second processor 4. The processor connection detector 341 includes a communication establishment detector 344 configured to detect whether communication with the second processor 4 has been established. In a case where the communication establishment detector 344 detects that the communication with the second processor 4 has been established, the processor connection detector 341 detects that the first processor 3 is connected with the second processor 4.

Based on a detection result of the processor connection detector 341, the mode selector 342 selects any of a standard mode and a compatible mode. The standard mode allows the processing inside the first processor 3 to correspond to the first imaging signal generated by the image sensor 21A of the first scope 2A. The compatible mode allows the processing inside the first processor 3 to correspond to a command transmitted from the second processor 4 and to the second imaging signal generated by the image sensor 21B received from the second processor 4. In a case where the processor connection detector 341 detects that the first processor 3 is connected with the second processor 4, that is, in a case where communication is established with the second processor 4, the mode selector 342 selects the compatible mode. In a case where the processor connection detector 341 detects that the first processor 3 is not connected with the second processor 4, the mode selector 342 selects the standard mode for processing the first imaging signal generated by the image sensor 21A of the first scope 2A inside the first processor 3, due to absence of connection with any other processor. In accordance with the selected mode, the mode selector 342 controls changeover processing of the changeover unit 35 (selector) to be described below.

In a case where the signal received from the second processor 4 with the first processor 3 functioning as a slave differs from the protocol of the signal to be output with the first processor 3 functioning as a master, to the server 7, the protocol converter 343 converts the received signal to the protocol of the signal to be output with the first processor 3 functioning as a master. Accordingly, the protocol converter 343 converts a command C2 output by the control unit 34 from the second protocol to the first protocol, and outputs a converted command C2-1 to the server 7. Note that in a case where the control unit 34 outputs the command C1 (refer to FIG. 2) from the control unit 34 to the server 7, protocol conversion is not needed since the output is performed in accordance with the first protocol.

The changeover unit 35 includes an electronic circuit for outputting solely one of the two input signals. Under the control of the mode selector 342, the changeover unit 35 selects, as an image signal to be output to the display device 6 and the recording image generator 37, any one of a first image signal G1 (refer to FIG. 2) based on the first imaging signal input from the image processing unit 31 and a second image signal G2 (refer to FIG. 1) based on the second imaging signal input from the converter 36 to be described below. In a case where the mode selector 342 selects the standard mode, the changeover unit 35 selects and outputs the first image signal G1 (refer to FIG. 2). In this case, the first image signal G1 is displayed on the display of the display device 6, and the first image signal G1 is input into the recording image generator 37. In a case where the mode selector 342 selects the compatible mode, the changeover unit 35 selects and outputs the second image signal G2 (refer to FIG. 1). In this case, the second image signal G2 is displayed on the display of the display device 6, and the second image signal G2 is input into the recording image generator 37.

The converter 36 converts the second imaging signal input from the second processor 4 so as to have a same format as the first image signal G1 after the image processing by the image processing unit 31 and outputs the converted signal to the changeover unit 35.

The recording image generator 37 generates a release image signal and a moving image signal for recording by performing codec processing on the image signal output from the changeover unit 35. Upon receiving a moving image generation instruction signal from the control unit 34, the recording image generator 37 generates (by encoding) a moving image signal of a predetermined format from a series of continuous image signals output from the changeover unit 35 and outputs the generated signal to the server 7. Upon receiving a release signal from the control unit 34, the recording image generator 37 generates release image data from the image signal output from the changeover unit 35, and outputs the generated release image data to the server 7.

In a case where the mode selector 342 selects the standard mode, the changeover unit 35 outputs the first image signal G1 (refer to FIG. 2). Accordingly, the recording image generator 37 generates a recording image signal G1' such as moving image data or release image data based on the first image signal G1. In a case where the mode selector 342 selects the compatible mode, the changeover unit 35 outputs the second image signal G2 (refer to FIG. 1). Accordingly, the recording image generator 37 generates a recording image signal G2' such as moving image data or release image data based on the second image signal G2. In a case where the mode selector 342 selects the compatible mode, the processing inside the first processor 3 is controlled so as to correspond to the command transmitted from the second processor 4. Accordingly, the recording image generator 37 generates moving image data or release image data from the second image signal G2 in accordance with the release signal or the moving image generation instruction signal transmitted from the second processor 4. In other words, in a case where the mode selector 342 selects the compatible mode, the recording image generator 37 generates the recording image signal G2' such as moving image data or release image data from the second image signal G2 in accordance with the release signal or the moving image generation instruction signal input by operation on the operation switch unit 23B of the second scope 2B.

The storage unit 38 includes a volatile memory and a non-volatile memory, and stores various programs for operating the first processor 3. The storage unit 38 temporarily stores the information being processed by the first processor 3. The storage unit 38 stores the first imaging signal output from the first scope 2A. The storage unit 38 may also be formed with a memory card, or the like, attached from outside of the first processor 3.

The second scope 2B is detachably attached to the second processor 4 (refer to FIG. 1). The second processor 4 generates the second image signal G2 by performing predetermined image processing on the second imaging signal transmitted from the attached second scope 2B. The second processor 4 is communicably connected to the first processor 3 and inputs the generated second image signal G2 into the external video image input port 33 of the first processor 3. The second processor 4 includes the image processing unit 41, a panel switch unit 42, the control unit 43, a recording image generator 44, and a storage unit 45.

The image processing unit 41 performs predetermined image processing on the second imaging signal generated by the image sensor 21B of the second scope 2B. Similarly to the image processing unit 31, the image processing unit 41 generates the second image signal by performing optical black subtraction (OB) processing, demosaicing processing, white balance (WB) adjustment processing, electronic zoom processing, edge enhancement processing, mask processing, on-screen display (OSD) processing, or the like, on the second imaging signal (digital) generated by the image sensor 21B, and outputs the generated second image signal after converting it into a format that can be displayed on a display device (not illustrated) determined as a set with the second processor 4. There is a case where the second image signal G2 output from the image processing unit 41 has a data format different from the data format that can be displayed on the display device 6 connected to the first processor 3. Note that there is a case where the image processing unit 41, instead of the image sensor 21B, performs noise reduction processing, clamp processing, and A/D conversion processing on the second imaging signal (analog).

The panel switch unit 42 is a switch group provided on a front panel constituting a casing of the second processor 4. In a case where the second scope 2B is attached to the second processor 4, the panel switch unit 42 receives an input of signals for freeze, release, and image adjustment (emphasis, electronic enlargement, color tone, etc.) onto the in-vivo image captured by the second scope 2B, and outputs the received various signals to the control unit 43 (refer to FIG. 1).

Similarly to the control unit 34, the control unit 43 includes a CPU and controls processing operation of each of portions of the second processor 4 by performing operation including transfer of instruction information and data to each of components of the second processor 4. In a case where the second scope 2B is attached to the second processor 4, the control unit 43 is connected to the image sensor 21B and the memory 22B of the second scope 2B via individual cables, and controls the image sensor 21B and the memory 22B. The control unit 43 is communicably connected to the first processor 3 via a cable. Communication is performed between the second processor 4 and the first processor 3 using the second protocol. The control unit 43 outputs to the control unit 34 a command corresponding to the release signal or the moving image generation instruction signal input by operation on the operation switch unit 23B of the second scope 2B with the protocol corresponding to the second processor 4. The control unit 43 transmits the various signals input from the panel switch unit 42 to the control unit 34 of the first processor 3 with the protocol corresponding to the second processor 4.

The recording image generator 44 includes the similar function as the recording image generator 37. In a case where the second processor 4 is communicably connected with the first processor 3 and the compatible mode is selected in the first processor 3, the recording image generator 37 in the first processor 3 generates a release image signal or a moving image signal from the second image signal. Accordingly, the recording image generator 44 does not execute generation processing of the release image signal or the moving image signal.

Similarly to the storage unit 38, the storage unit 45 is formed with a volatile memory, a nonvolatile memory, or the like, and stores various programs needed to operate the second processor 4 and imaging signals output from the second scope 2B, and in addition, temporarily stores information being processed by the second processor 4. The storage unit 45 may also be formed with a memory card, or the like, attached from outside of the second processor 4.

The input apparatus 5 includes an operation device such as a mouse, a keyboard and a touch panel. The input apparatus 5 receives input of various types of instruction information and inputs the received various types of instruction information to the control unit 34 of the first processor 3. In a case where the first processor 3 and the second processor 4 are communicably connected with each other, it receives input of various types of instruction information toward the second processor 4 and toward the second scope 2B attached to the second processor 4, and inputs the received instruction information to the control unit 34, in addition to the various types of instruction information toward the first processor 3.

The display device 6 includes a display using liquid crystal or organic electro luminescence (EL). The display device 6 displays various types of information including the display image output from the first processor 3. In the case of the standard mode, the display device 6 displays the first image signal G1 (refer to FIG. 2) based on the first imaging signal of the first scope 2A. In the case of the compatible mode, the display device 6 displays the second image signal G2 (refer to FIG. 1) based on the second imaging signal of the second scope 2B. With this configuration, the user can observe a desired position inside the subject and judge conditions by operating the first scope 2A and the second scope 2B while viewing an image (in-vivo image) displayed by the display device 6. Note that, under the control of the control unit 34, the display of the display device 6 also displays information indicating whether the actually displayed in-vivo image is obtained by the first scope 2A or the second scope 2B.

The server 7 is connected with the first processor 3 via a network, or the like, and communicates with the first processor 3. The server 7 includes a database (not illustrated), and records and manages various types of information including identification information of the release image signal, the moving image signal, and the image signals output by the first processor 3, in a database.

Figure 3:
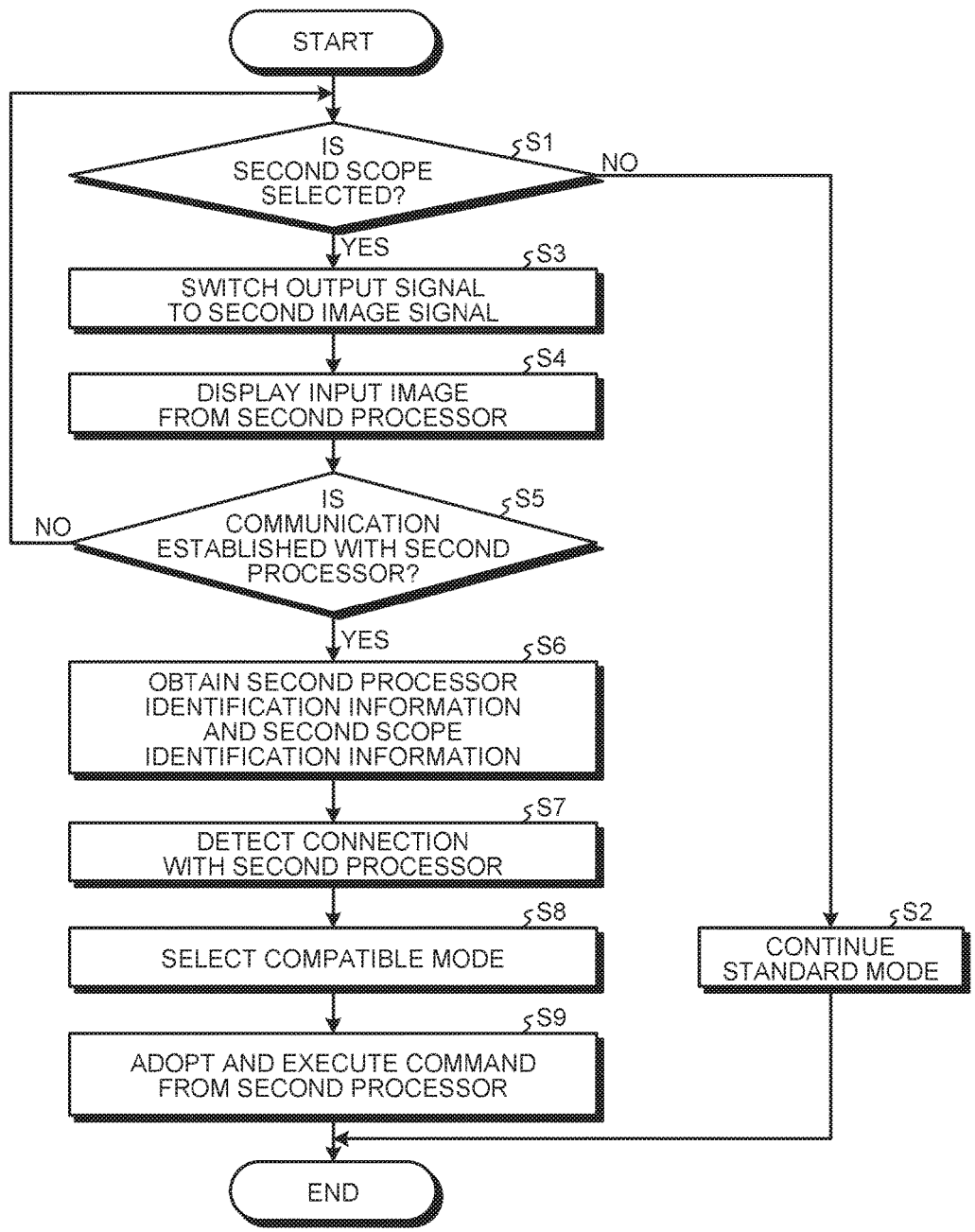
FIG. 3 is a flowchart illustrating setting of a standard mode or a compatible mode by a control unit of a first processor illustrated in FIGS. 1 and 2 and a processing procedure of control processing of internal processing of the first processor in accordance with individual modes.

FIG. 3 is a flowchart illustrating setting of a standard mode or a compatible mode by the control unit 34 of the first processor 3 and a processing procedure of control processing of internal processing of the first processor 3 in accordance with individual modes. Note that the first processor 3 has the standard mode being set as default, and the image signal output from the changeover unit 35 is the first image signal G1 based on the first imaging signal obtained by the first scope 2A.

As illustrated in FIG. 3, the control unit 34 determines whether the second scope 2B is selected as the scope to be used (Step S1). The control unit 34 determines that the second scope 2B is selected in a case where there is an input of instruction information to indicate the selection of the second scope 2B from the input apparatus 5, an input of the scope switching instruction information from the operation switch unit 23B, or an input of instruction information, etc. to indicate the selection of the second scope 2B by operation on the panel switch unit 42 from the control unit 43 of the second processor 4. In a case where the control unit 34 determines that the second scope 2B is not selected (Step S1: No), the control unit 34 continues the standard mode (Step S2).

In contrast, in a case where the control unit 34 determines that the second scope 2B is selected (Step S1: Yes), the mode selector 342 causes the changeover unit 35 to switch the output signal to the second image signal G2 input from the converter 36 (Step S3). This operation allows the second image signal G2, that is, the input image from the second processor 4, to be displayed on the display device 6 (Step S4). Note that in the examples of FIGS. 1 and 2, the second image signal G2 has been converted by the converter 36 so as to have the data format similar to that of the first image signal G1 after undergoing image processing by the image processing unit 31, leading to appropriate execution of display of the second image signal G2 on the display device 6.

Subsequently, the communication establishment detector 344 determines whether communication is established between the first processor 3 and the second processor 4 (Step S5). In a case where the communication establishment detector 344 determines that communication is not established between the first processor 3 and the second processor 4 (Step S5: No), the control unit 34 returns to Step S1, and determines whether the second scope 2B is selected. In contrast, in a case where the communication establishment detector 344 determines that communication is established between the first processor 3 and the second processor 4 (Step S5: Yes), the control unit 34 obtains the identification information of the second processor 4 and the identification information of the second scope 2B by communicating with the second processor 4 (Step S6). Based on the identification information of the second processor 4 and the identification information of the second scope 2B obtained by the communication establishment detector 344, the processor connection detector 341 detects that the second processor 4 is connected with the first processor 3 (Step S7). In a case where the second processor 4 is a model that can be set to the compatibility mode on the first processor 3, the mode selector 342 selects the compatible mode (Step S8).

The control unit 34 controls processing inside the first processor 3 so as to adopt and execute the command transmitted from the second processor 4 (Step S9). In this case, the second image signal G2 from the second processor 4 is displayed on the parent screen of the display device 6, and when the release signal is input, the recording image generator 37 performs codec processing on the second image signal G2. That is, in a case where the release signal is input from the control unit 43 into the control unit 34, the control unit 34 causes the recording image generator 37 to generate the release image signal from the second image signal G2 output from the changeover unit 35. Subsequently, the control unit 34 causes the recording image generator 37 to output the generated release image signal to the server 7, and transmits to the server 7 a command for causing the release image signal output from the recording image generator 37 to be recorded in association with the identification information corresponding to the release image signal. With this operation, the release signal issued by pressing of the release button in the second scope 2B is output from the control unit 43 to the control unit 34 of the first processor 3. As a result, the release image signal is generated in the recording image generator 37 and output to the server 7. The image signal output to the server 7 is delayed as compared with the case where the release signal is output from the first scope 2A directly attached to the first processor 3. This prolongs a release time, that is, a freeze period needed to achieve an image capture of a picture without disturbance compared with the case of the standard mode.

Figure 4:
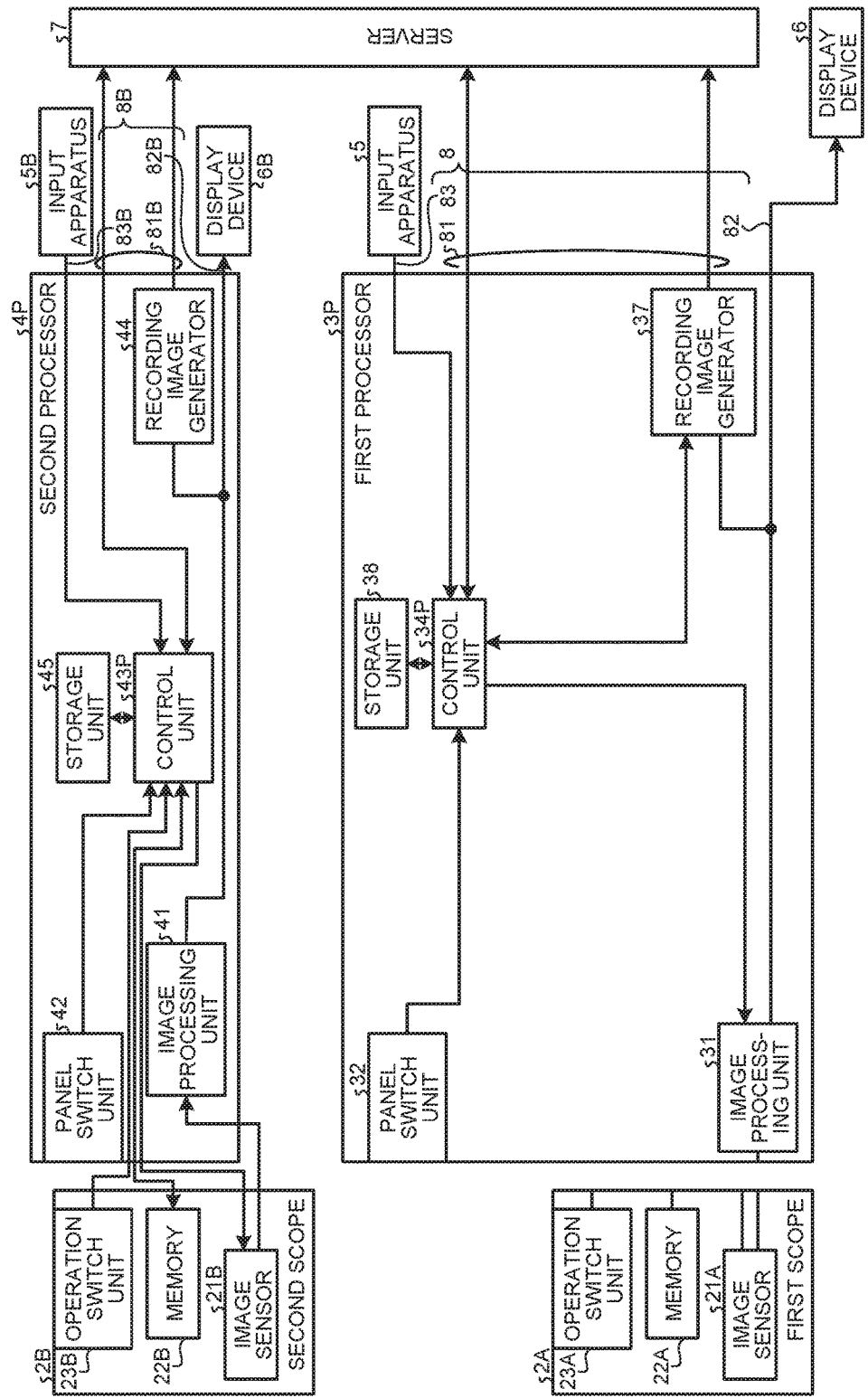
FIG. 4 is a schematic diagram illustrating a general configuration of an endoscope system in a conventional technique.

FIG. 4 is a schematic diagram illustrating a general configuration of an endoscope system in a conventional technique. In the conventional endoscope system, a first processor 3P and a second processor 4P, input apparatuses 5 and 5B, and display devices 6 and 6B are installed so as to correspond to the first scope 2A and the second scope 2B, respectively. Each of external devices corresponding to the first processor 3P is connected by a cable group 8 including cables 81 to 83 so as to be communicable with a control unit 34P of the first processor 3P. In addition, each of the external devices corresponding to the second processor 4 is connected by a cable group 8B including cables 81B to 83B which are separate from the cable group 8 so as to communicate with a control unit 43P of the second processor 4P. With the conventional configuration, the wiring structure between the devices is also complicated due to the use of two systems, leading to complication in operation, or the like, due to necessity of providing two input apparatuses and two display devices. Moreover, there is another proposed configuration in which the output of image signals to the display and the recording apparatus is performed by mutually connecting two processors with one of the processors functioning as a parent device and switching an image signal input path to the display or the recording apparatus on the parent device side to the side of one of the processors. This configuration, however, has a problem that it is difficult, in some cases, to perform communication with the display device or the recording apparatus corresponding to the version of the parent device side in a case where the version of the processor on the child device side is older, causing a failure in appropriately displaying or recording the image signal generated by the child device when it is output onto a display or the recording apparatus for the parent device.

In contrast, the first embodiment has a configuration in which the first scope 2A having the image sensor 21A is detachably attached to the first processor 3, while the first processor 3 is communicably connected with the second processor 4 on which the second scope 2B including the image sensor 21B is attached, and the control unit 34 controls processing inside the first processor 3 in accordance with the communication with the second processor 4. In other words, the control unit 34 allows the first processor 3 to have compatibility with the second processor 4 by allowing the processing inside the first processor 3 to correspond to the second image signal G2 input from the second processor 4 based on the command transmitted from the second processor 4 in accordance with the communication with the second processor 4.

Specifically, in a case where the second image signal G2 is input from the second processor 4, the second image signal G2 is converted to be able to be displayed on the display device 6, making it possible to also display the second image signal G2 appropriately on the display device 6 corresponding to the first processor 3. Moreover, in a case where a release signal is input from the second scope 2B, the recording image generator 37 in the first processor 3 generates a release image signal from the second image signal G2 input from the second processor 4, and outputs the generated release image signal from the first processor 3 to the server 7.

Furthermore, even in a case where the protocol of the command transmitted from the second processor 4 is different from the protocol between the first processor 3 and the server 7, the command is first protocol-converted inside the first processor 3 and then transmitted to the server 7. Accordingly, it is possible, even through the first processor 3, to allow the release image signal or the moving image signal based on the second image signal G2 input from the second processor 4 to be appropriately recorded onto the server 7. It is of course possible, in the first embodiment, to simplify the entire system configuration and prevent complication of operation compared with the conventional configuration illustrated in FIG. 4, because it is sufficient to provide one input apparatus 5 and one display device 6 corresponding to the first processor 3. Moreover, the first embodiment needs solely one cable system connecting the first processor 3 with the external device including the server 7, making it possible to simplify the wiring structure.

In this manner, according to the first embodiment, even in a case where the versions of the first processor 3 and the second processor 4 are different from each other, it is possible to share the input apparatus 5 and the display device 6 by the plurality of processors while simplifying the configuration of the entire endoscope system, and to appropriately record information output from the plurality of processors in a recording apparatus such as a server.

Figure 5:
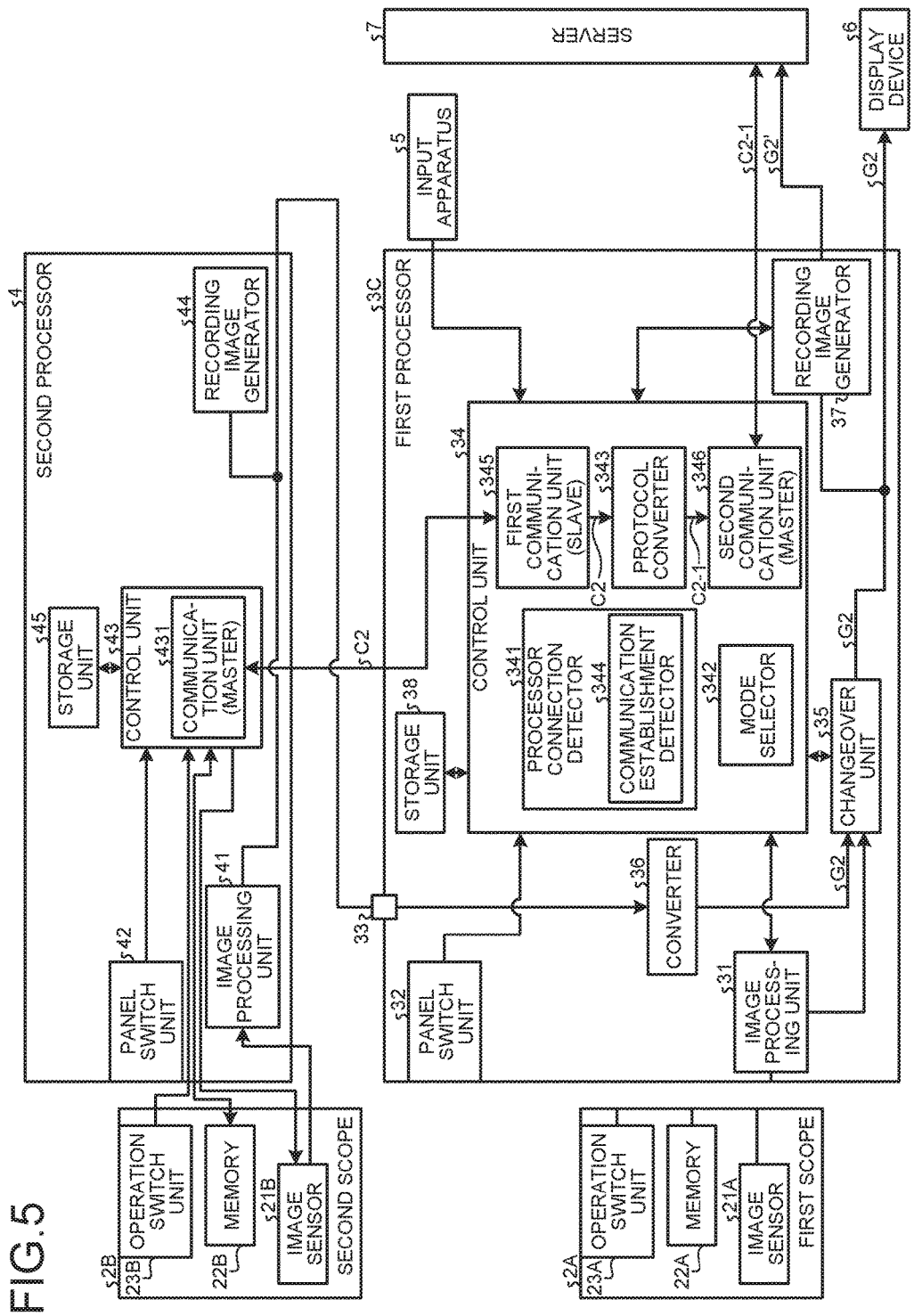
FIG. 5 is a schematic diagram for illustrating a configuration of the control unit of the first processor in the endoscope system according to the first embodiment of the present disclosure.

Now, the control unit 34 of the first processor 3 will be described in detail. FIG. 5 is a schematic diagram for illustrating a configuration of the control unit 34 of the first processor 3 in the endoscope system according to the first embodiment. A processor of the endoscope system performs communication by normally functioning as a master in a master-slave system in communication with the server, with the server functioning as a slave in a master-slave system. In the first embodiment, the first processor 3 functions as a master in communication with the server 7, and functions as a slave in communication with the second processor 4, enabling smooth communication with the second processor 4 and smooth communication with the server 7. In the first processor 3, the control unit 34 includes, in addition to the protocol converter 343, a first communication unit 345 and a second communication unit 346. The first communication unit 345 obtains, as a slave toward the second processor 4, a command C2 from the second processor 4. The second communication unit 346 transmits, as a master, the command C2-1 protocol-converted by the protocol converter 343 to the server 7. The second processor 4 includes a communication unit 431 that functions as a master in a master-slave system with the first communication unit 345 of the first processor 3. The protocol converter 343 converts the command C2 received by the first communication unit 345 as a slave from the control unit 43 of the second processor 4, from the second protocol to the first protocol. The second communication unit 346 transmits as a master the command C2-1 converted by the protocol converter 343 to the server 7.

In this manner, the first processor 3 functions as a master toward the server 7 and functions as a slave toward the second processor 4, and thus, can receive the command C2 transmitted from the second processor 4 with no problem.

First Modification of First Embodiment

Figure 6:
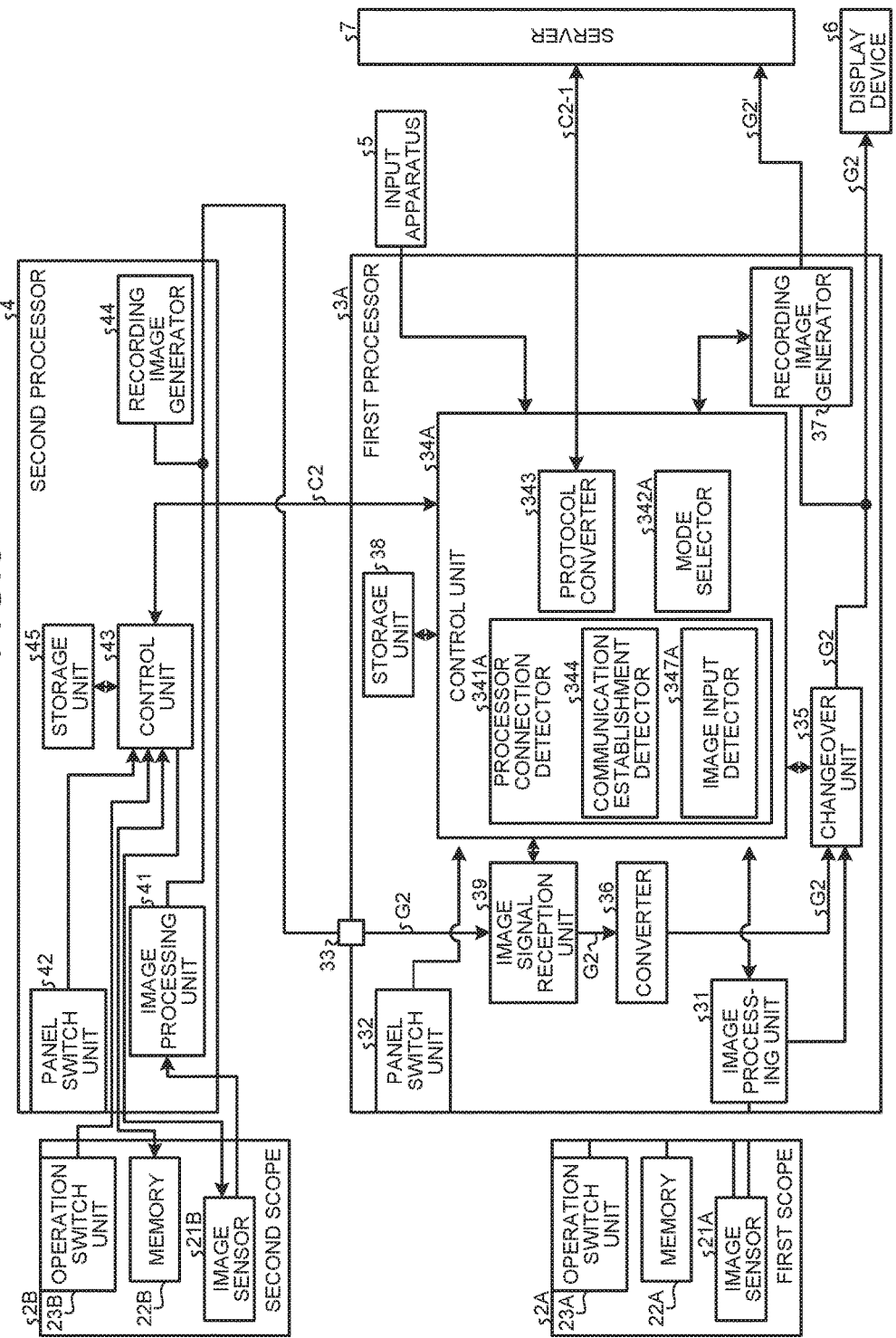
FIG. 6 is a schematic diagram illustrating a general configuration of an endoscope system according to a first modification of the first embodiment.

FIG. 6 is a schematic diagram illustrating a general configuration of an endoscope system according to a first modification of the first embodiment. As illustrated in FIG. 6, a first processor 3A in the first modification of the first embodiment includes a control unit 34A and further includes an image signal reception unit 39 as compared with the first processor 3 illustrated in FIGS. 1 and 2. The image signal reception unit 39 receives the second image signal G2 input from the external video image input port 33 and in a case where it has received the second image signal G2, the image signal reception unit 39 transmits reception information that indicates that it has received the second image signal G2 to the control unit 34A.

The control unit 34A includes a processor connection detector 341A, a mode selector 342A, and the protocol converter 343. The processor connection detector 341A further includes an image input detector 347A configured to detect an input of the second image signal G2 input from the second processor 4 into the first processor 3 based on the presence or absence of the reception information from the image signal reception unit 39. The mode selector 342A selects the compatible mode in a case where the processor connection detector 341A detects establishment of communication with the second processor 4 and detects the input of the second image signal G2 by the second processor 4 into the first processor 3.

Figure 7:
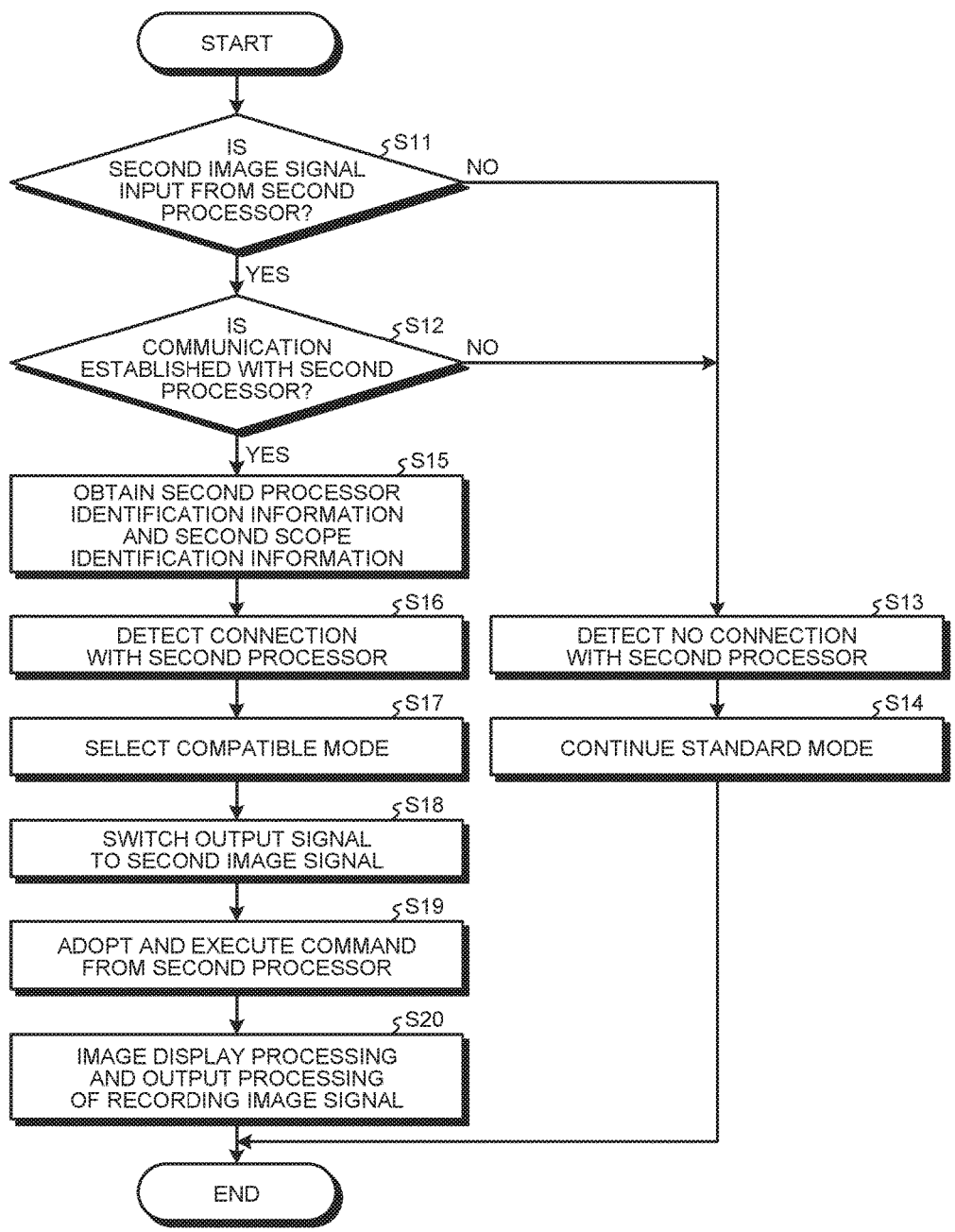
FIG. 7 is a flowchart illustrating setting of a standard mode or a compatible mode by the control unit of the first processor illustrated in FIG. 6 and a processing procedure of control processing of internal processing of the first processor in accordance with individual modes.

FIG. 7 is a flowchart illustrating setting of the standard mode or the compatible mode by the control unit 34A of the first processor 3A and a processing procedure of control processing of internal processing of the first processor 3A in accordance with individual modes.

As illustrated in FIG. 7, in the control unit 34A, the image input detector 347A detects the presence or absence of the input of the second image signal G2 from the second processor 4 into the first processor 3 based on the presence or absence of reception information from the image signal reception unit 39 (Step S11). In a case where the image input detector 347A detects the input of the second image signal G2 from the second processor 4 into the first processor 3 (Step S11: Yes), the communication establishment detector 344 determines whether communication has been established between the first processor 3 and the second processor 4 (Step S12).

In a case where the image input detector 347A has not detected the input of the second image signal G2 from the second processor 4 into the first processor 3 (Step S11: No), or where the communication establishment detector 344 determines that communication between the first processor 3 and the second processor 4 is not established (Step S12: No), the processor connection detector 341A detects that there is no connection from the second processor 4 to the first processor 3A (Step S13), and the control unit 34A continues the standard mode (Step S14).

In contrast, in a case where the communication establishment detector 344 determines that communication is established between the first processor 3 and the second processor 4 (Step S12: Yes), the control unit 34A obtains the identification information of the second processor 4 and the identification information of the second scope 2B by communicating with the second processor 4 (Step S15). Step S16 corresponds to Step S7 illustrated in FIG. 3. Step S17 corresponds to Step S8 illustrated in FIG. 3. Step S18 corresponds to Step S3 illustrated in FIG. 3. The control unit 34A adopts the command transmitted from the second processor 4 and executes processing inside the first processor 3 corresponding to the command (Step S19), and accordingly performs the image display processing onto the display device 6 or output processing of a recording image signal to the server 7 (Step S20). For example, upon receiving the release signal from the control unit 43 of the second processor 4, the control unit 34A causes the recording image generator 37 to generate a release image signal and output the generated release image signal to the server 7, and together with this, the control unit 34A transmits to the server 7 a command for recording the output release image signal.

As illustrated in the first modification of the first embodiment, it is allowable to cause the first processor 3A to establish communication with the second processor 4 and to configure to be able to automatically select the compatible mode in a case where the input of the second image signal G2 by the second processor 4 into the first processor 3 has been detected.

Second Modification of First Embodiment

Figure 8:
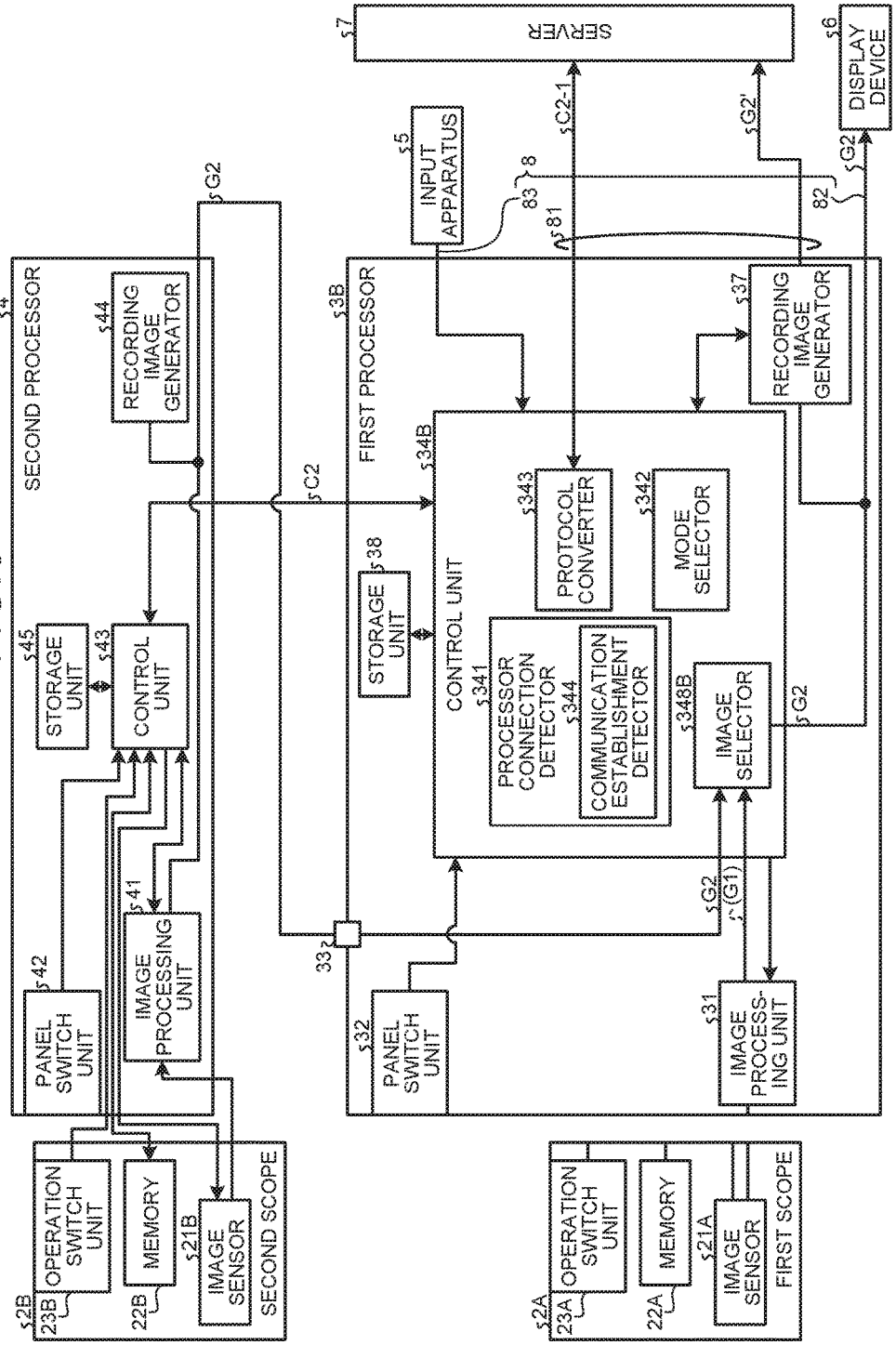
FIG. 8 is a schematic diagram illustrating a general configuration of an endoscope system according to a second modification of the first embodiment.

FIG. 8 is a schematic diagram illustrating a general configuration of an endoscope system according to a second modification of the first embodiment. Compared with the first processor 3 illustrated in FIGS. 1 and 2, a first processor 3B illustrated in FIG. 8 has a configuration in which the changeover unit 35 is deleted and the first image signal G1 output from the image processing unit 31 and the second image signal G2 output from the external video image input port 33 are directly input into an image selector 348B of a control unit 34B. In a case where the mode selector 342 selects the standard mode, the image selector 348B selects the first image signal G1 input from the image processing unit 31 and outputs the selected first image signal G1 to the display device 6 or the recording image generator 37. In a case where the mode selector 342 selects the compatible mode, the image selector 348B selects the second image signal G2 input from the external video image input port 33 and outputs the selected second image signal G2 to the display device 6 or the recording image generator 37. In the configurations illustrated in FIGS. 1 and 2, the hardware (changeover unit 35) is used as a portion of the selector to switch the image signals to be output to the display device 6 or the recording image generator 37. Alternatively, however, as in the configuration in FIG. 8, the image selector 348B of the control unit 34B including the CPU may select an image signal in accordance with a predetermined program and may output the image signal to the display device 6 or the recording image generator 37.

Third Modification of First Embodiment

Figure 9:
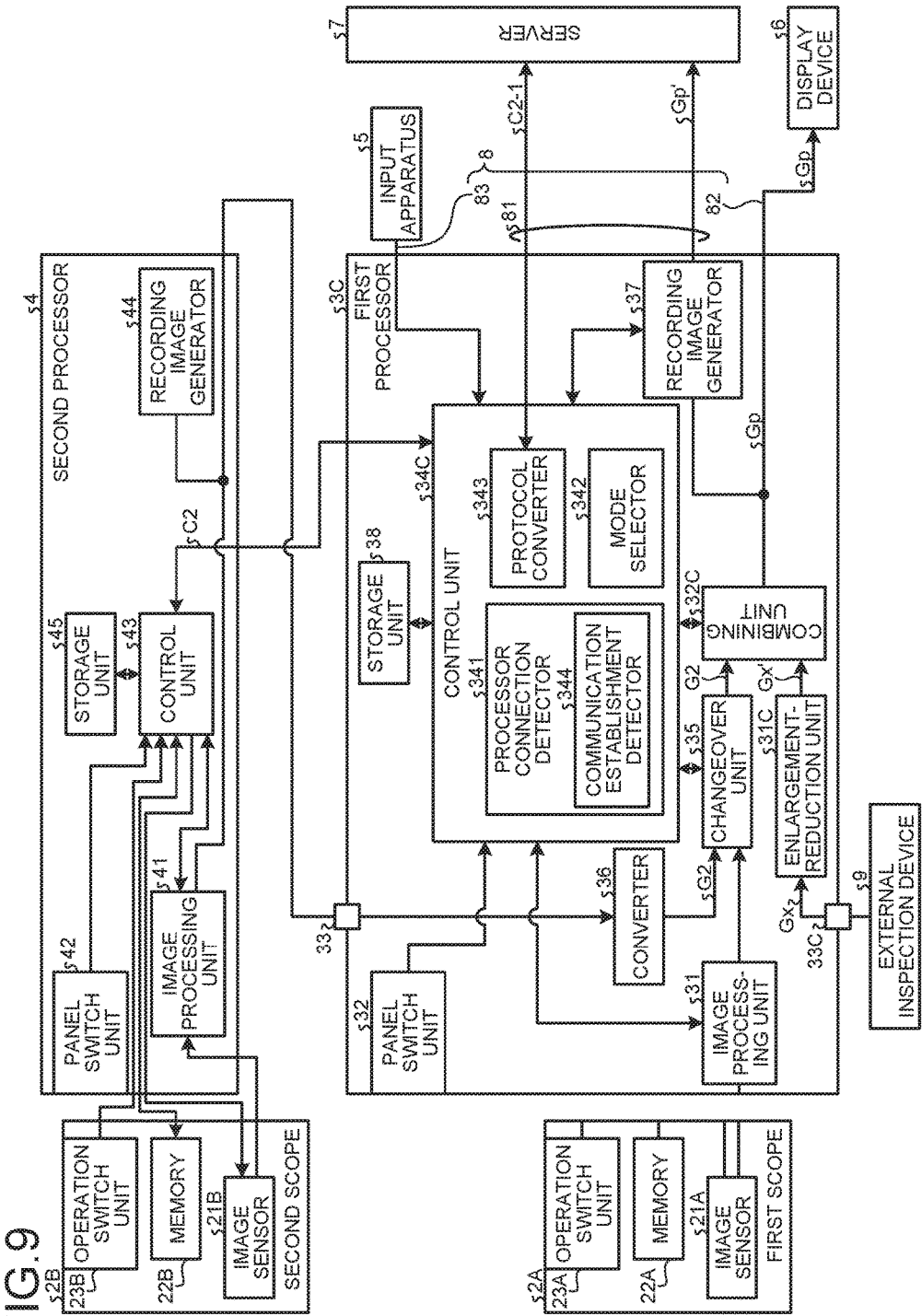
FIG. 9 is a schematic diagram illustrating a general configuration of an endoscope system according to a third modification of the first embodiment.

FIG. 9 is a schematic diagram illustrating a general configuration of an endoscope system according to a third modification of the first embodiment. A first processor 3C illustrated in FIG. 9 includes an inspection image input port 33C, an enlargement-reduction unit 31C, and a combining unit 32C. The inspection image input port 33C is communicably connected with an external inspection device 9, and an inspection image signal Gx is input from the external inspection device 9 into the inspection image input port 33C. The enlargement-reduction unit 31C performs enlargement processing or reduction processing on the inspection image signal Gx input from the inspection image input port 33C under the control of a control unit 34C. The combining unit 32C executes picture-in-picture (PinP) processing of generating a composed image Gp obtained by combining a first image signal G1 or a second image signal G2 output from the changeover unit 35 as a parent image with an enlarged or reduced inspection image signal Gx' output from the enlargement-reduction unit 31C as a child image. The recording image generator 37 generates a recording image signal Gp' from the composed image Gp output from the combining unit 32C. Examples of the external inspection device 9 include an X-ray inspection device or an ultrasonic inspection device.

As illustrated in the third modification of the first embodiment, it is possible to configure to select the first image signal G1 or the second image signal G2 corresponding to the scope being used and to display on the display device 6 a parent-child image obtained by combining the selected signal with the inspection image signal Gx input from the external inspection device 9.

Second Embodiment

Figure 10:
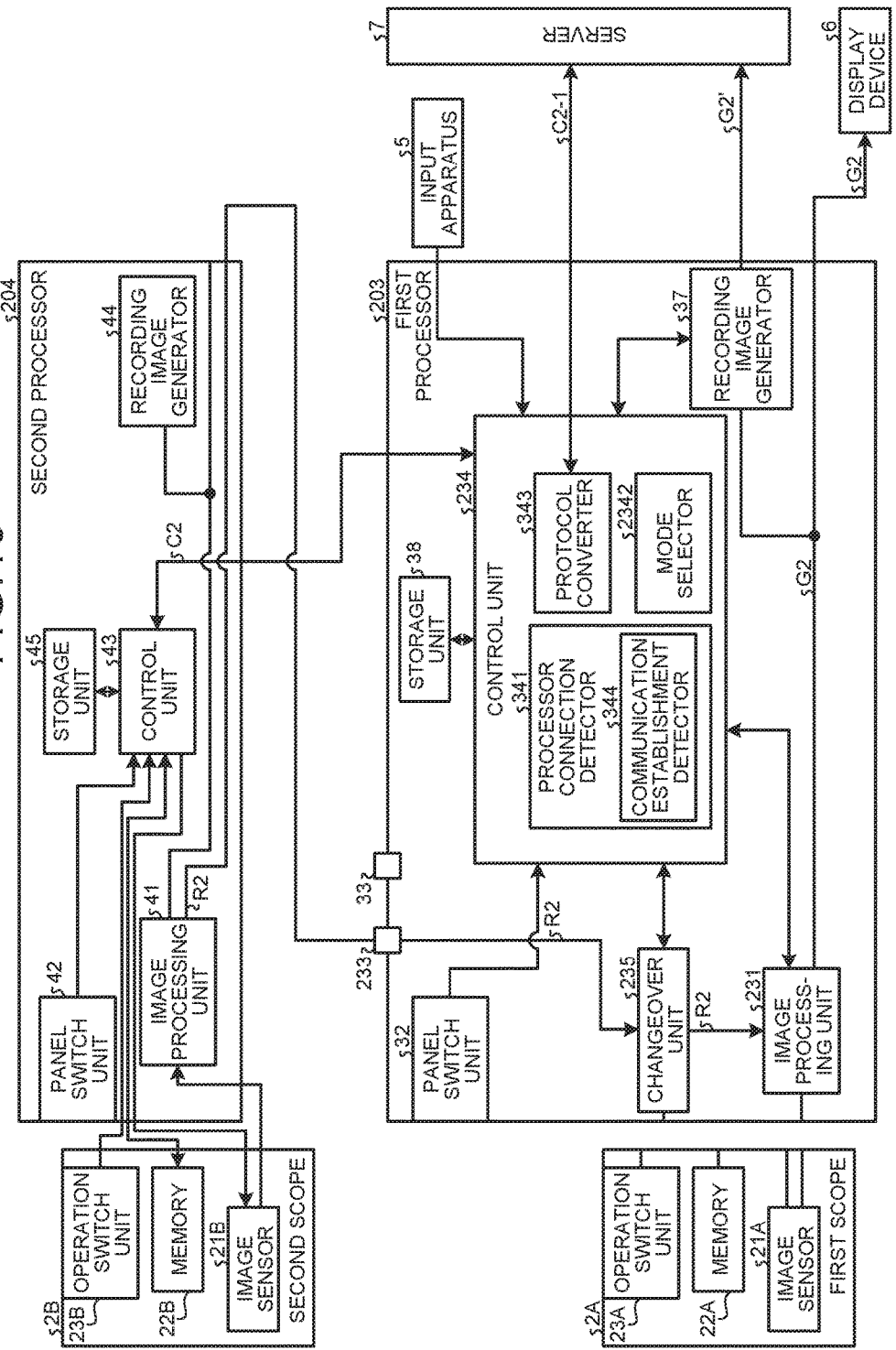
FIG. 10 is a schematic diagram illustrating a general configuration of an endoscope system according to a second embodiment.
Figure 11:
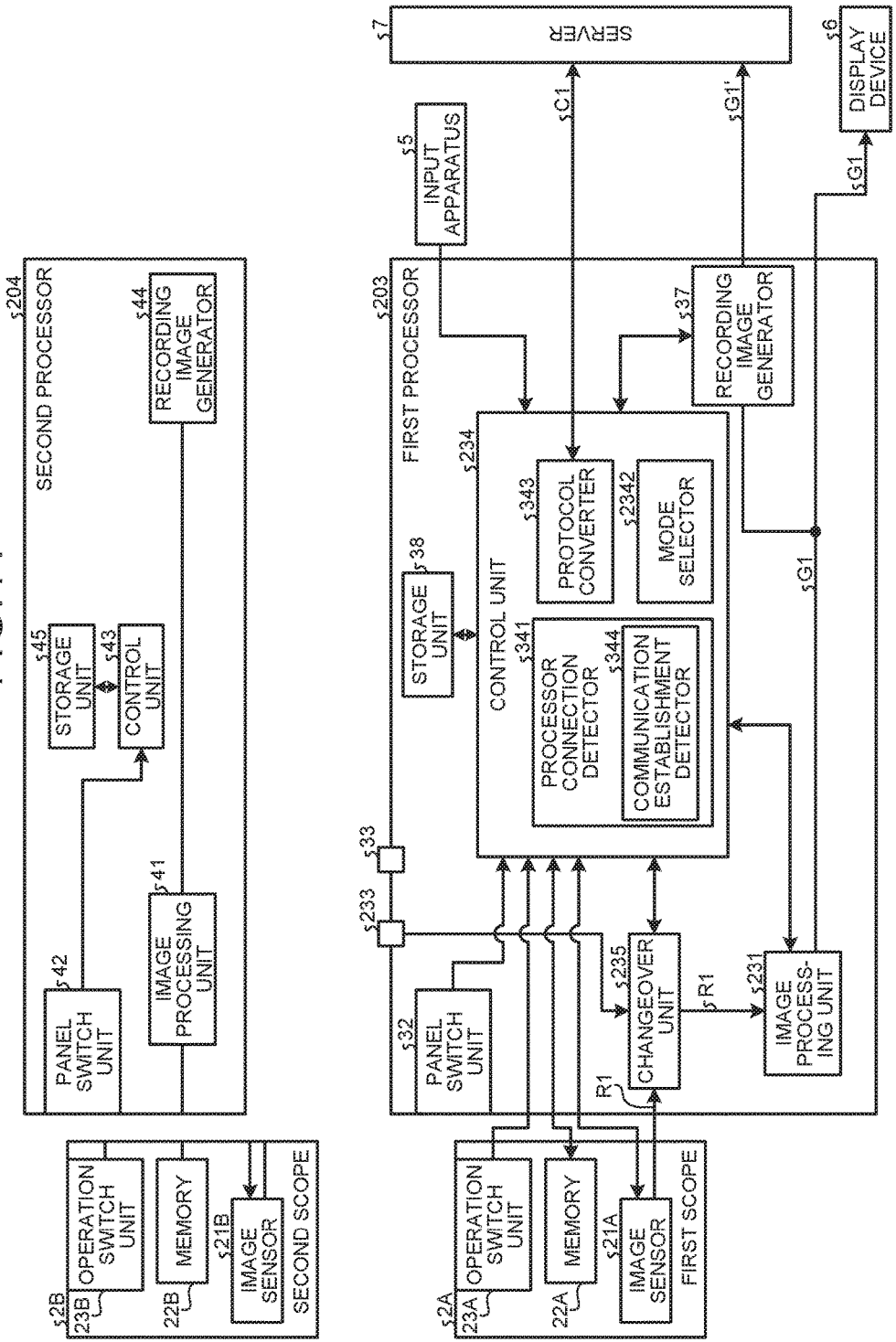
FIG. 11 is a schematic diagram illustrating a general configuration of the endoscope system according to the second embodiment.

Next, a second embodiment will be described. FIGS. 10 and 11 are schematic diagrams each illustrating a general configuration of an endoscope system according to the second embodiment.

As illustrated in FIGS. 10 and 11, the endoscope system according to the second embodiment includes a first processor 203 and a second processor 204 configured to output a second imaging signal R2 in the RAW data format from the image processing unit 41 and input the signal into the first processor 203.

Compared with the first processor 3, the first processor 203 includes an image processing unit 231, an external video image input port 233, a control unit 234, and a changeover unit 235.

For a first imaging signal R1 output from the first scope 2A (refer to FIG. 11) and input via the changeover unit 235, the image processing unit 231 outputs the first image signal G1 subjected to image processing corresponding to the first imaging signal R1. For the second imaging signal R2 (refer to FIG. 10) input via the external video image input port 233 and the changeover unit 235 to be described below, the image processing unit 231 outputs the second image signal G2 subjected to image processing corresponding to the second imaging signal R2. The first imaging signal R1 and the second imaging signal R2 are input into the image processing unit 231 in a RAW data format.

The second imaging signal R2 having the RAW data format output from the image processing unit 41 of the second processor 204 is input into the external video image input port 233 when the first processor 203 is connected with the second processor 204. In other words, similarly to the first imaging signal R1 input into the image processing unit 231, the second imaging signal R2 is input into the signal processing apparatus in the RAW data format.

The control unit 234 includes a mode selector 2342. Similarly to the mode selector 342 in FIGS. 1 and 2, the mode selector 2342 selects one of the standard mode and the compatible mode and causes the changeover unit 235 to switch the imaging signal to be output based on the presence or absence of establishment of communication between the first processor 203 and the second processor 204 detected by the processor connection detector 341. In a case where the mode selector 2342 selects the standard mode, the mode selector 2342 causes the changeover unit 235 to output the first imaging signal R1 and causes the image processing unit 231 to execute image processing corresponding to the first imaging signal R1 input from the changeover unit 235. In a case where the mode selector 2342 selects the compatible mode, the mode selector 2342 causes the changeover unit 235 to output the second imaging signal R2 and causes the image processing unit 231 to execute image processing corresponding to the second imaging signal R2 input from the changeover unit 235. The mode selector 2342 can distinguish the RAW data format of the second imaging signal R2 input from the image processing unit 231 by the communication with the second processor 204. Accordingly, in a case where the compatible mode is selected, the mode selector 2342 causes the image processing unit 231 to execute image processing appropriately corresponding to the data format of the second imaging signal R2 toward the second imaging signal R2 output from the changeover unit 235.

In a case where the mode selector 2342 selects the standard mode, the changeover unit 235 selects the first imaging signal R1 (refer to FIG. 11) and outputs it to the image processing unit 231. In a case where the mode selector 2342 selects the compatible mode, the changeover unit 235 selects the second imaging signal R2 (refer to FIG. 10) and outputs it to the image processing unit 231.

Figure 12:
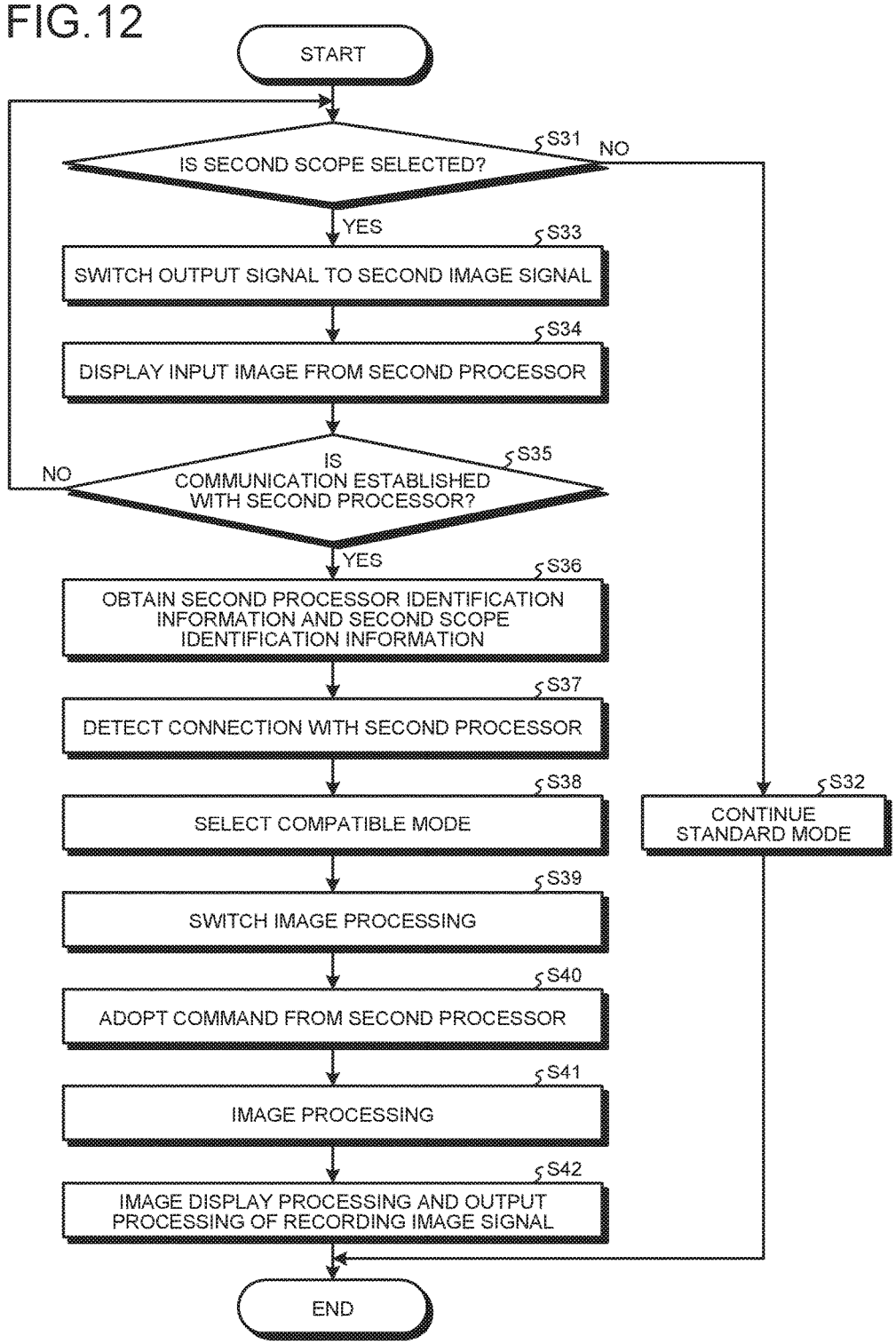
FIG. 12 is a flowchart illustrating setting of a standard mode or a compatible mode by the control unit of the first processor illustrated in FIGS. 10 and 11 and a processing procedure of control processing of internal processing of the first processor in accordance with individual modes.

FIG. 12 is a flowchart illustrating setting of the standard mode or the compatible mode by the control unit 234 of the first processor 203 and a processing procedure of control processing of internal processing of the first processor 203 in accordance with individual modes. Note that the first processor 203 has the standard mode being set as default, and the imaging signal output from the changeover unit 235 is the first imaging signal R1 output from the first scope 2A.

Steps S31 and S32 illustrated in FIG. 12 correspond to Steps S1 and S2 illustrated in FIG. 3, respectively. In a case where the control unit 234 determines that the second scope 2B is selected (Step S31: Yes), the mode selector 2342 causes the changeover unit 235 to switch the output signal to the second imaging signal R2 input from the external video image input port 233 (Step S33). This operation allows the second imaging signal R2 to be input into the image processing unit 231 and allows an image based on the second imaging signal R2, that is, the input signal from the second processor 204, to be displayed on the display device 6 (Step S34). Steps S35 to S38 correspond to Steps S5 to S8 illustrated in FIG. 3, respectively. The second imaging signal R2 is input from the changeover unit 235 into the image processing unit 231. Accordingly, along with the selection of the compatible mode in Step S38, the mode selector 2342 causes the image processing unit 231 to switch the image processing to the image processing corresponding to the input second imaging signal R2 (Step S39). The control unit 234 adopts the command transmitted from the second processor 204 (Step S40), causes the image processing unit 231 to execute image processing corresponding to the input second imaging signal R2 (Step S41) and performs image display processing on the display device 6 or output processing of the recording image signal to the server 7 in accordance with the command transmitted from the second processor 204 (Step S42).

In this manner, in the second embodiment, in a case where the compatible mode is selected in accordance with the communication with the second processor 204, the control unit 234 causes the changeover unit 235 to switch the output signal to the image processing unit 231 to the second imaging signal R2 input from the second processor 204 and controls the image processing unit 231 to perform processing corresponding to the second imaging signal R2. With this control, compatibility with the second processor 204 is given to the first processor 203, making it possible to achieve the similar effect as in the first embodiment. Furthermore, since the version of the first processor 203 is often newer than the version of the second processor 204, it is possible to cause the image processing unit 231 to perform new image processing difficult to be executed by the image processing unit 41 of the second processor 204, onto the second imaging signal R2 output from the second processor 204. This enables output of image signals appropriate for observation or recording.

First Modification of Second Embodiment

Figure 13:
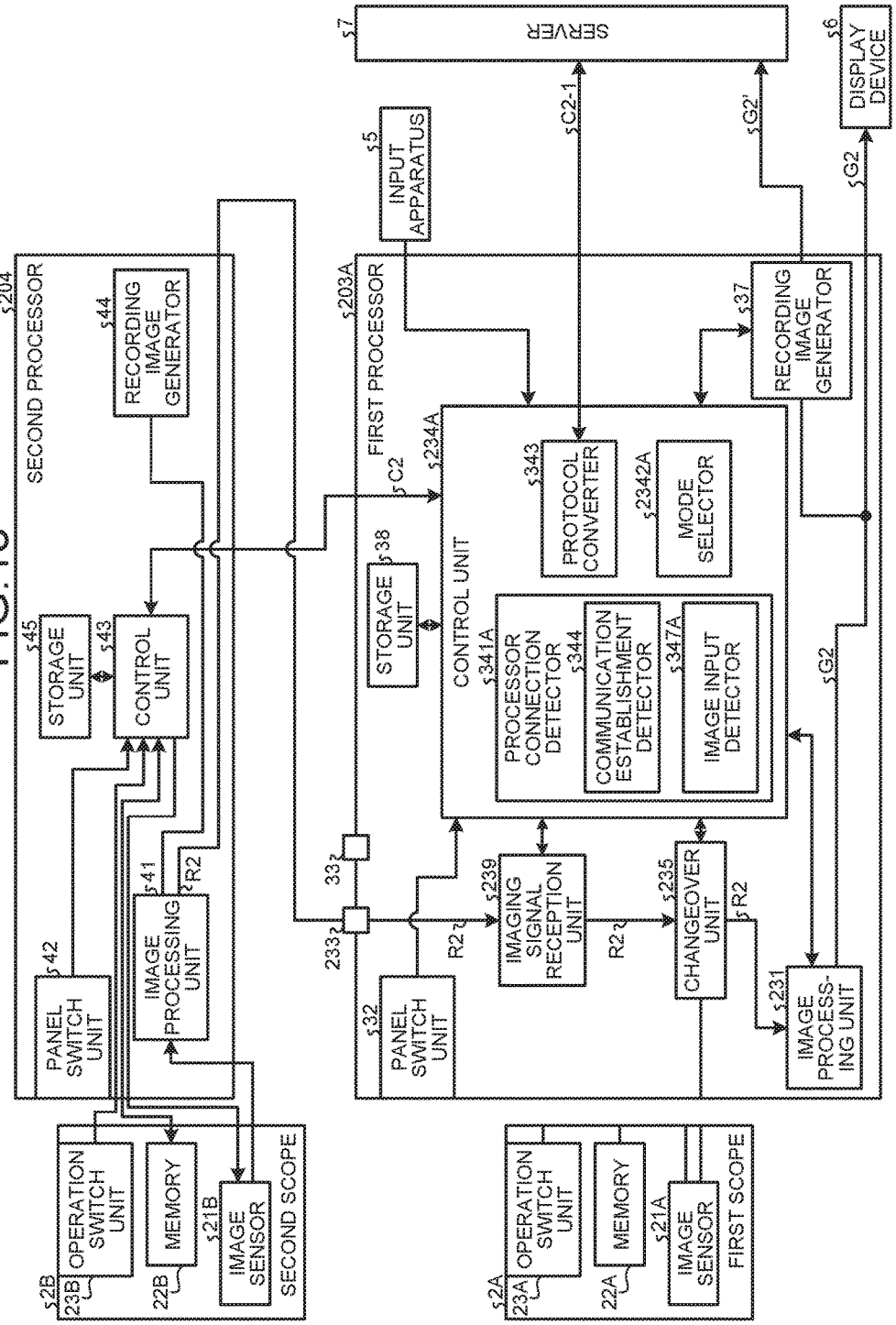
FIG. 13 is a schematic diagram illustrating a general configuration of an endoscope system according to a first modification of the second embodiment.

FIG. 13 is a schematic diagram illustrating a general configuration of an endoscope system according to a first modification of the second embodiment. A first processor 203A illustrated in FIG. 13 includes a control unit 234A and an imaging signal reception unit 239. The control unit 234A includes a processor connection detector 341A illustrated in FIG. 6 and a mode selector 2342A. The imaging signal reception unit 239 receives the second imaging signal R2 input from the external video image input port 233 and when it has received the second imaging signal R2, transmits reception information that indicates that it has received the second imaging signal R2 to the image input detector 347A of the control unit 234A. Similarly to the first processor 3A in FIG. 6, the mode selector 2342A selects the compatible mode in a case where the processor connection detector 341A detects establishment of communication with the second processor 204 and detects the input of the second imaging signal R2 by the second processor 204 into the first processor 203A.

FIG. 14 is a flowchart illustrating setting of the standard mode or the compatible mode by the control unit 234A of the first processor 203A and a processing procedure of control processing of internal processing of the first processor 203A in accordance with individual modes.

As illustrated in FIG. 14, in the control unit 234A, the image input detector 347A detects the presence or absence of the input of the second imaging signal R2 from the second processor 204 into the first processor 203A based on the presence or absence of reception information from the imaging signal reception unit 239 (Step S51). Steps S52 to S57 correspond Steps S12 to S17 illustrated in FIG. 7, respectively. Step S58 corresponds to Step S33 illustrated in FIG. 12. Steps S59 to S62 correspond to Steps S39 to S42 illustrated in FIG. 12, respectively.

As illustrated in the first modification of the second embodiment, it is allowable to cause the first processor 203A to establish communication with the second processor 204 and to configure to be able to automatically select the compatible mode in a case where the input of the second imaging signal R2 by the second processor 204 to the first processor 203A has been detected.

Moreover, in the second embodiment, similarly to the second modification of the first embodiment, the first imaging signal R1 output from the image sensor 21A and the second imaging signal R2 output from the external video image input port 233 may be directly input into the control unit 234, and the control unit 234 may select the imaging signal corresponding to the mode selection of the mode selector 2342 and may output the selected imaging signal to the image processing unit 231. In this case, in a case where the mode selector 2342 selects the standard mode, the control unit 234 selects the first imaging signal R1 and outputs it to the image processing unit 231, and also causes the image processing unit 231 to execute image processing corresponding to the first imaging signal R1. In contrast, in a case where the mode selector 2342 selects the compatible mode, the control unit 234 selects the second imaging signal R2 and outputs it to the image processing unit 231, and also causes the image processing unit 231 to execute image processing corresponding to the second imaging signal R2. In this manner, the control unit 234 including the CPU may select the imaging signal in accordance with a predetermined program and output the selected imaging signal to the image processing unit 231.

The execution programs for individual processing to be executed in the first processors 3, 3A to 3C, 203, and 203A, the second processors 4 and 204, and in other components, according to the first and second embodiments, may be recorded and provided in a computer readable recording medium such as a CD-ROM, a flexible disk, a CD-R and a digital versatile disk (DVD) in a file with installable or executable format. Alternatively, the program may be stored on a computer connected to a network such as the Internet and may be supplied by downloading the program via the network. It is also allowable to provide or distribute the program via a network including the Internet.

According to the present disclosure, it is possible to output an appropriately processed image while achieving a simplified configuration of the entire endoscope system.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A first signal processing apparatus to which a first endoscope apparatus including a first image sensor is detachably attached, the first signal processing apparatus being communicably connected with a second signal processing apparatus to which a second endoscope apparatus including a second image sensor is attached and also connected with an external device other than the second signal processing apparatus, the first signal processing apparatus being configured to process a first imaging signal generated by the first image sensor or a second imaging signal generated by the second image sensor, the first signal processing apparatus comprising:
  a control unit configured to:
    process the first imaging signal when a first command is received;
    when a second command is received, control the process inside the first signal processing apparatus to make the process of the second imaging signal to correspond to the second command; and
    select one of:
    a standard mode in which the process inside the first signal processing apparatus corresponds to the first imaging signal generated by the first image sensor; and
    a compatible mode in which the process inside the first signal processing apparatus corresponds to the second imaging signal generated by the second image sensor and received from the second signal processing apparatus;
  a slave communication unit configured to communicate, as a slave node of a second master-slave system, with the second signal processing apparatus in accordance with a second communication protocol for the second master-slave system;
  a protocol converter configured to convert the second command, which is received by the control unit through the slave communication unit, into a command that follows a first communication protocol for a first master-slave system;
  a master communication unit configured to communicate, as a master node of the first master-slave system, with the external device in accordance with the first communication protocol, and to transmit the command resulted by the protocol converter to the external device;

a selector configured to select and output the first imaging signal between the first imaging signal and the second imaging signal when the first imaging signal and the second imaging signal have been input and the control unit selects the standard mode, and configured to select and output the second imaging signal when the first imaging signal and the second imaging signal have been input and the control unit selects the compatible mode;

an image processing unit configured to perform image processing corresponding to the first imaging signal on the first imaging signal and output the image-processed first imaging signal and configured to perform image processing corresponding to the second imaging signal on the second imaging signal and output the image-processed second imaging signal; and a recording image generator configured to generate a still image signal for recording or a moving image signal for recording from the input imaging signal, wherein the second imaging signal has a data format similar to the data format of the first imaging signal input into the image processing unit, wherein the selector is configured to output the imaging signal, out of the first imaging signal and the second imaging signal, that corresponds to the mode selected by the control unit to the image processing unit, wherein the control unit is configured to cause the image processing unit to execute the image processing corresponding to the first imaging signal output from the selector when the control unit has selected the standard mode and causes the image processing unit to execute the image processing corresponding to the second imaging signal output from the selector when the control unit has selected the compatible mode, and wherein, when the control unit has selected the compatible mode and has received a recording image generation command from the second signal processing apparatus, the control unit causes the recording image generator to generate the still image signal for recording or the moving image signal for recording from the second imaging signal.

2. The first signal processing apparatus according to claim 1, wherein the image processing unit is configured to input into the selector the first imaging signal in a format that can be displayed on a display device connected with the first signal processing apparatus, wherein the second imaging signal has been subjected to predetermined image processing by the second signal processing apparatus, and wherein the selector is configured to output the imaging signal, out of the first imaging signal and the second imaging signal, that corresponds to the mode selected by the control unit to a display device connected with the first signal processing apparatus.

3. The first signal processing apparatus according to claim 2, further comprising a converter configured to convert the second imaging signal input from the second signal processing apparatus into a data format similar to the format of the first imaging signal subjected to the image processing by the image processing unit and output the converted second imaging signal to the selector.

4. The first signal processing apparatus according to claim 1, wherein the control unit is configured to select the compatible mode when communication with the second signal processing apparatus is established.

5. The first signal processing apparatus according to claim 4, wherein the control unit is configured to detect an input of the second imaging signal input from the second signal processing apparatus, into the first signal processing apparatus, and select the compatible mode when the communication with the second signal processing apparatus is established.

6. An endoscope system comprising: the first signal processing apparatus according to claim 1: the second signal processing apparatus; and the external device.

* * * * *